US006977291B2

(12) United States Patent
Sunkara et al.

(10) Patent No.: US 6,977,291 B2
(45) Date of Patent: Dec. 20, 2005

(54) PRODUCTION OF POLYTRIMETHYLENE ETHER GLYCOL AND COPOLYMERS THEREOF

(75) Inventors: Hari B. Sunkara, Wilmington, DE (US); Leo E. Manzer, Wilmington, DE (US)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 883 days.

(21) Appl. No.: 09/738,688

(22) Filed: Dec. 15, 2000

(65) Prior Publication Data

US 2002/0007043 A1 Jan. 17, 2002

Related U.S. Application Data

(60) Provisional application No. 60/172,264, filed on Dec. 17, 1999.

(51) Int. Cl.[7] ............................................. C08G 65/34
(52) U.S. Cl. ...................................... 528/425; 568/619
(58) Field of Search ........................... 568/619; 528/425

(56) References Cited

U.S. PATENT DOCUMENTS

| | | | |
|---|---|---|---|
| 2,492,955 A | 1/1950 | Ballard et al. | |
| 2,520,733 A | 8/1950 | Morris et al. | 260/615 |
| 3,023,192 A | 2/1962 | Shivers, Jr. et al. | 260/75 |
| 3,027,352 A | 3/1962 | Wailing et al. | 260/67 |
| 3,326,985 A | 6/1967 | Mason | 260/615 |
| 3,384,623 A | 5/1968 | Inoue et al. | 260/75 |
| 3,651,014 A | 3/1972 | Witsiepe | 260/75 |
| 3,763,109 A | 10/1973 | Witsiepe | 260/75 |
| 4,277,577 A | 7/1981 | Burg et al. | 525/154 |
| 4,482,750 A | 11/1984 | Hetzel et al. | 568/621 |
| 4,937,314 A | 6/1990 | Greene | 528/272 |
| 4,970,295 A | 11/1990 | Schuchardt | 528/416 |
| 5,064,935 A | 11/1991 | Jackson et al. | |
| 5,070,178 A | 12/1991 | Yamada | 528/272 |
| 5,128,185 A | 7/1992 | Greene | 428/36.9 |
| 5,403,912 A | 4/1995 | Gunatillake et al. | 528/425 |
| 5,434,239 A | 7/1995 | Bhatia | |
| 5,552,513 A | 9/1996 | Bhatia | |
| 5,599,900 A | 2/1997 | Bhatia | |
| 5,659,089 A | 8/1997 | Cai et al. | 568/619 |
| 5,786,443 A | 7/1998 | Lowe | |
| 6,235,948 B1 | 5/2001 | Sunkara et al. | 568/868 |
| 2002/0010374 A1 | 1/2002 | Sunkara et al. | |

FOREIGN PATENT DOCUMENTS

| | | |
|---|---|---|
| EP | 0 385 632 | 9/1990 |
| WO | WO 94/09055 | 4/1994 |
| WO | WO 96/13540 | 5/1996 |
| WO | WO 99/01496 | 1/1999 |
| WO | WO 00/10953 | 3/2000 |

OTHER PUBLICATIONS

U.S. Appl. No. 09/638,356, filed Aug. 15, 2000.
U.S. Appl. No. 09/727,792, filed Dec. 1, 2000.
S. V. Conjeevaram, R. S. Benson & D. J. Lyman, "Block Copolyurethanes Based on Polyoxytrimethylene Glycols", Journal of Polymer Science, Polymer Chemistry Edition, 1985; vol. 23; pp 429–444.
Cesar Carlos Gonzalez, Antonio Bello, Jose Manuel Perena, "Oligomerization of Oxetane and Synthesis of Polyterephthalates Derived from 1,2–Propanediol and 3.3'–Oxydipropanol", Makromol. Chem. 190, No. 6; Jun. 1989; pp 1217–1224.
Pathiraja A. Gunatillake, Gordon F. Meijs, Ronald C. Chatelier, Donna M. McIntosh & Ezio Rizzardo, "Synthesis and Characterization of Hydroxy–Terminated Poly(Alkylene Oxides) by Condensation Polymerization of Diols", Polymer International, 1992; vol. 27, No. 3; pp 275–283.
Simon J. McCarthy, Gordon F. Meijs, Pathiraja Gunatillake, "Synthesis, Characterization, and Stability of Poly[(alkylene oxide) ester] Thermoplastic Elastomers", 1997: pp 1319–1332.
M. Younus Qureshi & Matthias Ochel, "Synthesis and Characterization of High Molecular Weight Poly(Trimethylene Oxide)", Pergamon, 1996; vol. 32, No. 6; pp 691–693.
Milton J. Rhoad & Paul J. Flory, "The Synthesis of Polymeric Ethers", Contribution No. 169 from The Goodyear Tire and Rubber Co., Research Laboratory, May 1950; vol. 72; pp 2216–2219.
International Search Report from counterpart application PCT/US 00/34202.
Written Opinion from PCT/US 00/34202.
International Preliminary Examination Report from PCT/US 00/34202.

*Primary Examiner*—James J. Seidleck
*Assistant Examiner*—Irina S. Zemel

(57) ABSTRACT

A process for the manufacture of polytrimethylene ether glycol comprising the steps of: (a) providing (1) 1,3-propanediol reactant selected from the group consisting of 1,3-propanediol and/or oligomers or prepolymers of 1,3-propanediol having a degree of polymerization of 2–9 and mixtures thereof, and (2) a polycondensation catalyst; and (b) polycondensing the 1,3-propanediol reactant to form a polytrimethylene ether glycol at less than one atmosphere pressure, and the product of the process. In addition, polytrimethylene ether glycol has a number average molecular weight greater than 1,500, an APHA color of less than 120, an unsaturation of less than 20 meq/kg, and a content of cyclic ether oligomers of less than 2%.

87 Claims, No Drawings

PRODUCTION OF POLYTRIMETHYLENE ETHER GLYCOL AND COPOLYMERS THEREOF

PRIORITY

This application claims priority from U.S. provisional patent application Ser. No. 60/172,264, filed Dec. 17, 1999, which is incorporated herein by reference.

FIELD OF THE INVENTION

This invention concerns a process for the preparation of polytrimethylene ether glycols from 1,3-propanediol reactant.

TECHNICAL BACKGROUND OF THE INVENTION

Known polyalkylene ether glycols include polyethylene glycol, poly-1,2- and 1,3-propylene ether glycol, polytetramethylene ether glycol, polyhexamethylene ether glycol and copolymers thereof. They have been used widely as lubricants or as starting materials for preparing lubricants used in the molding of rubbers and in the treatment of fibers, ceramics and metals. They have also been used as starting materials for preparing cosmetics and medicines, as starting materials or additives for water-based paints, paper coatings, adhesives, cellophane, printing inks, abrasives and surfactants and as starting materials for preparing resins, such as alkyd resins. They have also been used as soft, flexible segments in the preparation of copolymers and segmented copolymers such as polyurethanes, thermoplastic polyesters and unsaturated polyester resins. Examples of commercially important polyether glycols include polyethylene glycol, poly(1,2-propylene glycol), ethylene oxide/propylene oxide copolyols, and polytetramethylene ether glycol.

Among the polyether glycols, the most widely used polyether glycol is poly(1,2-propylene glycol) (PPG) because of its low cost. This polymer is non-crystalline, liquid at room temperature and hence easy to handle. However, PPG has secondary hydroxyl end groups and it contains high percentages of terminal unsaturation.

Polyoxytrimethylene glycol or polytrimethylene ether glycol or poly(1,3-propylene glycol) can be derived either from 1,3-propanediol or from oxetane. These polytrimethylene ether glycols have primary hydroxyl groups and have low melting points and are highly flexible.

U.S. Pat. No. 2,520,733, which is incorporated herein by reference, discloses polymers and copolymers of trimethylene glycol and a process for the preparation of these polymers from trimethylene glycol in the presence of a dehydration catalyst such as iodine, inorganic acids (e.g., sulfuric acid) and organic acids. The trimethylene glycol derived polymers disclosed in this patent are dark brown or black in color. The color can be improved to a light yellow color by treatment processes disclosed therein. Polymers of molecular weight from about 100 to about 10,000 are mentioned; however, there is a preference for molecular weights of 200–1,500 and the highest molecular weight shown in the examples is 1096.

U.S. Pat. No. 3,326,985, which is incorporated herein by reference, discloses a process for forming a polytrimethylene glycol having an average molecular weight of 1,200–1,400. First, polytrimethylene glycol which has an average molecular weight of about 900 is formed using hydriodic acid. This is followed by an after treatment which comprises vacuum stripping the polyglycol at a temperature in the range of 220–240° C. and at a pressure of 1–8 mm Hg in a current of nitrogen from 1–6 hours. The product is stated to be useful in preparing polyurethane elastomers. There is also presented a comparative example directed to producing polytrimethylene glycol with a molecular weight of 1,500.

U.S. Pat. No. 5,403,912, which is incorporated herein by reference, disclosed a process for the polymerization of polyhydroxy compounds, including alkanediols having from 2–20 carbon atoms, in the presence of an acid resin catalyst at temperatures of from 130–220° C. Molecular weights of from 150 to 10,000 are mentioned. A copolymer of 1,10-decanediol and 1,3-propanediol having a number average molecular weight of 2050 was exemplified.

Preparation of ester terminated polyethers and hydroxy terminated polyethers from oxetanes and or mixtures of oxetanes and oxolanes by ring opening polymerization is disclosed U.S. Pat. No. 4,970,295, which is incorporated herein by reference. The resulting polyethers are stated to have molecular weights in the range of 250–10,000, preferably 500–4,000. Synthesis of polyoxytrimethylene glycols from oxetane is also described in S. V. Conjeevaram, et al., Journal of Polymer Science: Polymer Chemistry Ed., Vol. 23, pp 429–44 (1985), which is incorporated herein by reference.

It is desirable to prepare said polyether glycol from readily available materials, not, for example, from the commercially unavailable oxetane. The polytrimethylene ether glycols heretofore obtained from the polycondensation of 1,3-propanediol are of low molecular weight, are highly discolored and/or require long reaction times. Therefore, an efficient process that produces polytrimethylene ether glycol with little or no color, and desired molecular weight, has been sought.

SUMMARY OF THE INVENTION

This invention is directed to a process for the manufacture of polytrimethylene ether glycol comprising the steps of:

a) providing (1) 1,3-propanediol reactant selected from the group consisting of 1,3-propanediol and/or oligomers or prepolymers of 1,3-propanediol having a degree of polymerization of 2–9 and mixtures thereof, and (2) a polycondensation catalyst; and b) polycondensing the 1,3-propanediol reactant to form a polytrimethylene ether glycol at less than one atmosphere pressure.

In one preferred embodiment, the 1,3-propanediol reactant is selected from the group consisting of 1,3-propanediol and/or dimer and trimer of 1,3-propanediol and mixtures thereof. In another preferred embodiment, the 1,3-propanediol reactant is selected from the group consisting of the 1,3-propanediol or the mixture containing at least 90 weight % of 1,3-propanediol. In yet another preferred embodiment, the 1,3-propanediol reactant is 1,3-propanediol.

The polycondensation is preferably carried out at a temperature of at least 150° C., more preferably at least 160° C., even more preferably at least 170° C., and most preferably at least 180° C. The polycondensation is preferably carried out at a temperature of up to 250° C., preferably up to 220° C., and even more preferably up to 210° C.

In a preferred embodiment, the process is carried out in batch mode. The invention can be carried out in sequential batch mode.

In another preferred embodiment, the process is carried out in continuous mode.

The polycondensing pressure preferably is less than 500 mm Hg (66 kPa), more preferably is less than 250 mm Hg (33 kPa), even more preferably is less than 100 mm Hg (13 kPa) and most preferably is less than 50 mm Hg (6.6 kPa). Polycondensation can be carried out at less than 5 mm Hg (660 Pa) and even at less than 1 mm Hg (130 Pa).

In one preferred embodiment, the polycondensation catalyst is homogeneous. In another preferred embodiment, the polycondensation catalyst is heterogeneous. Preferably, the catalyst is selected from the group consisting of Lewis Acid, Bronsted Acid, super acid, and mixtures thereof. More preferably, the catalyst is selected from the group consisting of inorganic acids, organic sulfonic acids, heteropolyacids, and metal salts. Most preferably, the catalyst is selected from the group consisting of sulfuric acid, fluorosulfonic acid, phosphorous acid, p-toluenesulfonic acid, benzenesulfonic acid, phosphotungstic acid, phosphomolybdic acid, trifluoromethanesulfonic acid, 1,1,2,2-tetrafluoroethanesulfonic acid, 1,1,1,2,3,3-hexafluoropropanesulfonic acid, bismuth triflate, yttrium triflate, ytterbium triflate, neodymium triflate, lanthanum triflate, scandium triflate and zirconium triflate. The catalyst can also be selected from the group consisting of zeolites, fluorinated alumina, acid-treated silica, acid-treated silica-alumina, heteropolyacids and heteropolyacids supported on zirconia, titania, alumina and/or silica. The most preferred catalyst is sulfuric acid.

In one embodiment, the resulting polytrimethylene ether glycol is purified by hydrolyzing the acid esters present in the polymer chain and removing at least one of unreacted glycol, and linear and cyclic ether oligomer.

Depending on end use, the polytrimethylene ether glycol number average molecular weight (Mn) is preferably greater than 1,000, 1,500, 1,650 or 2,000 and less than 5,000, 4,950, 4,000 or 3,500.

The dispersity of the polytrimethylene ether glycol is preferably within the range of 1.5 to 2.1. In a preferred embodiment, the process further comprises purifying the polytrimethylene ether glycol to a dispersity of 1.5 to 2.1.

The polytrimethylene ether glycol preferably has an APHA color of less than 120, more preferably less than 100, and most preferably less than 50.

Preferably, the polytrimethylene ether glycol has an unsaturation of less than 20 meq/kg., more preferably less than 15 meq/kg. In a preferred embodiment, the process further comprises purifying the polytrimethylene ether glycol to an unsaturation of less than 20 meq/kg., more preferably less than 15 meq/kg.

The polytrimethylene ether glycol preferably has a content of cyclic ether oligomers of less than 2%, more preferably less than 1%. In a preferred embodiment, the process further comprises purifying the polytrimethylene ether glycol to a cyclic ether oligomer content less than 1%.

The reaction mixture can comprise up to 50 mole %, based on all diols present, of a comonomer diol other than oligomers of 1,3-propanediol. Preferred comonomer diols are 2-methyl-1,3-propanediol, 2,2-dimethyl-1,3-propanediol, 2,2-diethyl-1,3-propanediol, 1,6-hexanediol, 1,8-octanediol, 1,10-decanediol, 1,12-dodecanediol and mixtures thereof. More preferred as comonomers are 2-methyl-1,3-propanediol, 2,2-dimethyl-1,3-propanediol, and 2,2-diethyl-1,3-propanediol. Preferably, when present, the comonomers comprises 1–20 mole %, based on all diols present.

The catalyst (e.g., solid catalyst) is preferably used in a concentration in the range of 0.1 to 20 weight %, by weight of the reaction mixture. Soluble catalyst is preferably used in an amount of no more than 5 weight %.

Sulfuric acid is preferably used at a concentration of from 0.1 to 5 weight %, by weight of the reaction mixture, more preferably from 0.25–2.5 weight %.

Preferably, the process is carried out with the 1,3-propanediol and it has a purity greater than 99%. In another preferred embodiment, the process is carried out with the 1,3-propanediol and up to 10% of the low molecular weight oligomers.

In a particularly preferred embodiment, the polytrimethylene ether glycol has a number average molecular weight of 1,500–4,950 and an APHA color of less than 120, the pressure in the reduced pressure stage is less than 250 mm Hg (33 kPa) and the polycondensation temperature is 170–190° C.

The invention is also directed to a process for the manufacture of polytrimethylene ether glycol comprising the steps of:

a) providing (1) 1,3-propanediol and (2) a polycondensation catalyst;

b) condensing 1,3-propanediol to form oligomer or prepolymer of 1,3-propanediol having a degree of polymerization of 2–9 or a mixture comprising one or more thereof; and c) polycondensing the oligomer or prepolymer of 1,3-propanediol having a degree of polymerization of 2–9 or a mixture comprising one or more thereof, to form a polytrimethylene ether glycol at less than one atmosphere pressure.

Preferably, step b) is carried out at about atmospheric pressure, the pressure in step c) is less than 300 mm Hg (40 kPa), the temperature in step b) is 150–210° C. and the temperature in step c) is 170–250° C. More preferably, the temperature of step b) is 170–210° C. and the temperature of step c) is 180–210° C. Preferably, in step b), 1,3-propanediol is condensed to dimer and trimer. Preferably, the pressure for step c) is less than 250 mm Hg (33 kPa) and the polytrimethylene ether has a number average molecular weight of 1,650 to 4,950.

The invention is also directed to a polytrimethylene ether glycol produced by any of these processes. Preferably, the polytrimethylene ether glycol has a number average molecular weight of greater than 1,650.

In addition, the invention is directed to polytrimethylene ether glycol having a number average molecular weight greater than 1,500, an APHA color of less than 120, an unsaturation of less than 20 meq/kg, and a content of cyclic ether oligomers of less than 2%. The polytrimethylene ether glycol of the invention preferably has a dispersity of 1.5 or more and preferably has a dispersity of 2.1 or less, and preferably has an alkalinity in the range of −5 to +5, more preferably −2 to +1, preferably has a number average molecular weight of from 1,650 to 4,000, and preferably has an APHA color of less than 100, an unsaturation of less than 15 meq/kg and a cyclic ether content of less than 1%.

DETAILED DESCRIPTION OF THE INVENTION

This invention relates to synthesis of trimethylene ether glycol polymers and copolymers by the acid-catalyzed polycondensation (this reaction is also referred to as a dehydration reaction at times) of 1,3-propanediol reactant.

Herein, "1,3-propanediol reactant" means 1,3-propanediol and/or oligomers or prepolymers of 1,3-propanediol having a degree of polymerization of 2–9 and mixtures thereof; "oligomer" is used to refer to dimer and trimer of 1,3-propanediol; and "prepolymer" is used to refer to 1,3-propanediol based compounds having a degree of polymerization of 4–9. Herein, when referring to "polytrimethylene ether glycol" or copolymer, reference is made to polymers or copolymers having a Mn of 1000 or more.

Polytrimethylene ether glycol is sometimes referred to as "polyoxytrimethylene glycol" or "3G polyol", and 1,3-propanediol is sometimes referred to as "trimethylene glycol" or "3G".

The polycondensation can be carried out in one or more stages wherein at least one of the stages is performed under reduced pressure, that is, pressure of less than 1 atmosphere (760 mm Hg, 101 kPa).

The polycondensation may be carried out in batch, sequential batch (i.e., a series of batch reactors) or continuous modes in any of the equipment customarily employed for continuous processes. The condensate water is preferably removed from the reaction mass with the aid of an inert gas purge (preferably using nitrogen).

The temperature of the process is controlled in order to obtain a good yield of the desired product. Preferably, the temperature is at least 150° C., more preferably at least 160° C., still more preferably at least 170° C., and most preferably at least 180° C. Preferably the temperature is no greater than 250° C., more preferably no greater than 220° C., and most preferably no greater than 210° C.

In one preferred embodiment, the process of the present invention is carried out in a two-stage batch mode wherein the first stage is condensation carried out at about one atmosphere and the second stage is polycondensation carried out at reduced pressure. The first stage condensation reaction is carried out at about one atmosphere in order to avoid losing 1,3-propanediol due to application of a vacuum. The first stage of the reaction is carried out in order to convert some or all of the 1,3-propanediol to oligomers or prepolymers, preferably oligomers (dimer and trimer), which due to their higher boiling points are not removed by vacuum. The second stage is polycondensation of 1,3-propanediol reactants, preferably the oligomers.

In the two-stage batch mode, the first stage of the process is preferably carried out at 150° C. to 210° C., more preferably 170° C. to 210° C. The second is preferably carried out at 170° C. to 250° C., more preferably 180° C. to 210° C.

In another preferred embodiment, the process is carried out in continuous mode. Here, the temperature range is preferably as specified above with respect to the general conditions, with 150–250° C. being preferred, 170–220° C. more preferred, and 180 to 210° C. most preferred. Preferred continuous processes are described in U.S. patent application Ser. No. 09/738,689, filed concurrently herewith (now U.S. Pat. No. 6,720,459 B2), and the provisional patent application No. 60/172,126, filed Dec. 17, 1999, both of which are incorporated herein by reference.

The polycondensation reaction is carried out under reduced pressure, i.e., less than 1 atm (760 mm Hg). Pressure is linked to temperature and thus can vary. Lower temperatures typically require lower pressures and higher temperatures typically permit operation at higher pressure. When the polycondensation is performed at a temperature of less than 220° C., the preferred pressure is less than 500 mm Hg (66 kPa); at a temperature of 150° C., the preferred pressure is 100 mm Hg (13 kPa) or less.

In general, the polycondensation pressure is preferably less than 250 mm Hg (33 kPa), more preferably less than 100 mm Hg (13 kPa), still more preferably less than 50 mm Hg (6.6 kPa), and most preferably less than 5 mm Hg (660 Pa) in the reduced pressure reaction stage(s). Pressures of less than 1 mm Hg (130 kPa) can also be used.

For the two-stage batch process or other similar batch processes involving multiple stages, the polycondensation reaction pressure is preferably less than 250 mm Hg (33 kPa).

When operated as a continuous process, the polycondensation pressure is preferably less than specified above, most preferably less than 250 mm Hg (33 kPa), or lower.

Whether as a batch or continuous process, the pressure can be decreased as the reaction progresses. Preferably pressure will be constant at least within each stage, once steady state has been reached in a continuous process.

Pressures of greater than 1 atmosphere (101 kPa), and even 50 psi (340 kPa) or more can also be used when there are at least 2 stages to the process. Typically higher pressures are used at the beginning or in the early stages of the reaction process and lower pressures (vacuum) are used in the latter stages. Lower pressures near the end of the reaction aid completion to desired Mn and low polymer color. If a multi-stage reaction process is employed, the pressure in stages after the first can be as low as 0.1 mm Hg (13 kPa).

The catalysts used in the process of the present invention are dehydration polycondensation catalysts. The preferred homogeneous polycondensation catalysts are those acids with a pKa less than about 4, preferably with a pKa less than about 2, and include inorganic acids, organic sulfonic acids, heteropolyacids, perfluoroalkyl sulfonic acids and mixtures thereof. Also preferred are metal salts of acids with a pKa less than about 4, including metal sulfonates, metal trifluoroacetates, metal triflates, and mixtures thereof including mixtures of the salts with their conjugate acids. Specific examples of catalysts include sulfuric acid, fluorosulfonic acid, phosphorous acid, p-toluenesulfonic acid, benzenesulfonic acid, phosphotungstic acid, phosphomolybdic acid, trifluoromethanesulfonic acid, 1,1,2,2-tetrafluoroethanesulfonic acid, 1,1,1,2,3,3-hexafluoropropanesulfonic acid, bismuth triflate, yttrium triflate, ytterbium triflate, neodymium triflate, lanthanum triflate, scandium triflate, zirconium triflate. A preferred catalyst is sulfuric acid.

Preferred heterogeneous catalysts are zeolites, acid-treated silica, acid-treated silica-alumina, acid-treated clays, heterogeneous heteropolyacids and sulfated zirconia.

Catalyst precursors may also be employed. For example, 1,3-dibromopropane yields, after reaction with 1,3-propanediol, hydrogen bromide which then functions as a dehydration catalyst. Similar results are obtained with 1,3-diiodopropane and other dihaloalkanes.

Generally, catalyst concentrations are typically about 0.1% or more, by weight of the 1,3-propanediol reactant, more preferably about 0.25% or more, and preferably used in a concentration of about 20% or less, by weight of the reaction mixture, more preferably 10% or less, even more preferably 5% of less, and most preferably 2.5% or less. Catalyst concentrations can be as high as 20 weight % for heterogeneous catalysts and lower than 5 weight % for soluble catalysts.

The process of the present invention will provide polytrimethylene ether glycol with improvements in molecular weight, reaction times, and polymer color. The starting material for the present process can be any 1,3-propanediol reactant or a mixture thereof. The quality of the starting material is important for producing high quality polymer. The 1,3-propanediol employed in the process of the present invention may be obtained by any of the various chemical routes or by biochemical transformation routes. Preferred routes are described in U.S. Pat. Nos. 5,015,789, 5,276,201, 5,284,979, 5,334,778, 5,364,984, 5,364,987, 5,633,362, 5,686,276, 5,821,092, 5,962,745 and 6,140,543, U.S. patent application Ser. Nos. 09/346,418 (now U.S. Pat. No. 6,277, 289), Ser. No. 09/382,970 (now U.S. Pat. No. 6,342,646), Ser. No. 09/382,998 (now U.S. Pat. No. 6,284,930) and Ser. No. 09/505,785 (now U.S. Pat. No. 6,331,264), and WO 98/57913, 00/10953 and WO 00/14041, all of which are incorporated herein by reference. Preferably the 1,3-propanediol has a purity of greater than 99%. The 1,3-propanediol-based starting materials may be purified prior to use, for example by treatment with an acid catalyst at an elevated temperature and reaction time to react impurities into forms that can be separated as described in WO 00/10953, which is incorporated herein by reference.

In some instance, it may be desirable to use up to 10% or more of low molecular weight oligomers where they are available. Thus, preferably the starting material consists essentially of 1,3-propanediol diol and dimer and trimer thereof. The most preferred starting material is comprised of 90 weight % or more 1,3-propanediol, more preferably 99 weight % or more.

The starting material for the present process can contain up to 50% by weight (preferably 20 weight % or less) of comonomer diols in addition to the 1,3-propanediol and/or its oligomers. Comonomer diols that are suitable for use in the process include aliphatic diols, for example 1,6-hexanediol, 1,7-heptanediol, 1,8-octanediol, 1,9-nonanediol, 1,10-decanediol, 1,12-dodecanediol, 3,3,4,4,5,5-hexafluro-1,5-pentanediol, 2,2,3,3,4,4,5,5-octafluoro-1,6-hexanediol, 3,3,4,4,5,5,6,6,7,7,8,8,9,9,10,10-hexadecafluoro-1,12-dodecanediol, cycloaliphatic diols, for example 1,4-cyclohexanediol, 1,4-cyclohexanedimethanol and isosorbide, polyhydroxy compounds, for example glycerol, trimethylolpropane, and pentaerythritol. A preferred group of comonomer diol is selected from the group consisting of 2-methyl-1,3-propanediol, 2,2-dimethyl-1,3-propanediol, 2,2-diethyl-1,3-propanediol, 2-ethyl-2-(hydroxymethyl)-1,3-propanediol, 1,6-hexanediol, 1,8-octanediol, 1,10-decanediol, isosorbide, and mixtures thereof. Thermal stabilizers, antioxidants and coloring materials may be added to the polymerization mixture or to the final polymer if necessary.

When 1,3-propanediol is polymerized by the process of this invention, wherein at least one stage is carried out under reduced pressure rather than at atmospheric pressure several improvements result. One notable advantage is that the discoloration of the polyether glycol decreases significantly. For example, heating 1,3-propanediol in the presence of 1 wt % sulfuric acid at 175° C. for 8 hours under vacuum resulted in a polymer having much lower color value than the polymer obtained under atmospheric pressure (Table 1). Furthermore, polytrimethylene ether glycol produced under the reduced pressure embodiment had a number average molecular weight much greater than shown with respect to published polycondensation reactions.

The polyether glycol prepared by the process of the present invention can be purified further to remove the acid present by means known in the art. It should be recognized that in certain applications the product may be used without further purification. However, the purification process described below improves the polymer quality and functionality significantly and it is comprised of (1) a hydrolysis step to hydrolyze the acid esters that are formed during the polymerization and (2) typically (a) water extraction steps to remove the acid, unreacted monomer, low molecular weight linear oligomers and oligomers of cyclic ethers (OCE), (b) a solid base treatment to neutralize the residual acid present and (c) drying and filtration of the polymer to remove the residual water and solids. The properties of the refined polytrimethylene ether glycols are provided in Table 2 (Examples 4 and 5).

The process of this invention provides a high purity, high molecular weight polymer of polytrimethylene ether glycol having a number average molecular weight (Mn) of at least 1,000, more preferably at least 1,500, even more preferably at least 1,650 and most preferably 2,000. The Mn is preferably less than 5000 (e.g., preferably 4,950 or less), more preferably less than 4,000, and most preferably less than 3,500. The aforementioned purification process may be used to increase molecular weight further. The polymer after purification has essentially no acid end groups. For a polymer having a number average molecular weight of 2350, the hydroxyl number is 47.5.

Advantageously, the polymer (prior to any post purification) has an APHA color of less than 120, preferably less than 100 and more preferably less than 50. The polymer (after any post purification) has a low unsaturation of less than 20 meq/kg, preferably less than 15 meq/kg. There is also an OCE content (prior to any post purification) of less than 2%, preferably (after any post purification) less than 1%. The dispersity (after any post purification) of the polytrimethylene ether glycol is within the range of 1.5 to 2.1. The polytrimethylene ether glycol (after any post purification) has an alkalinity in the range of −5 to +5, preferably in the range of −2 to +1.

The invention is demonstrated in the following examples, which are not intended to be limiting, wherein all parts, percentages and the like are by weight, unless indicated otherwise.

EXAMPLES

A commercial grade quality of 1,3-propanediol which is available from E. I. du Pont de Nemours and Company (Wilmington, Del.) was used in the examples below. The purity of this raw material is >99.8%. 2-Methyl-1,3-propanediol (98%) from Lyondell (Houston, Tex.) and neopentyl glycol (99%) from Aldrich were used as received. The crude and purified polytrimethylene ether glycols were analyzed by methods known in the art. The number-average molecular weights of polytrimethylene ether glycol were determined either by analyzing end-groups using NMR spectroscopic method or by titration. Hydroxyl number was determined according to ASTM E222 method and is the way that should be used to analyze whether something is within the scope of this invention. Polydispersity (Mw/Mn) of the polymer was measured by GPC. Depending upon the intensity of the color of the samples to be measured, two different color scales were used. For light colored products, Platinum-Cobalt (APHA) Standard (ASTM D1209) and for dark colored products Gardner Standard (ASTM D154) were used. Melting, crystallization and glass transition temperatures of the polymer were obtained from differential scanning calorimetry. Unsaturation in polyether glycols was determined by ASTM D-4671. Alkalinity of the polymer sample was measured by known internal standard method. Quantification of the OCE in polyether samples was done using the GC/AED technique and compound independent technique monitoring the carbon 496 nm emission line for carbon using 2-methyl-1,3-propanediol as an internal standard. ASTM method D445-83 and ASTM method D792-91 were used to determine the absolute (dynamic) viscosity and density of the polymer, respectively.

Example 1

Preparation of Polytrimethylene Ether Glycol Using Sulfuric Acid Catalyst

A 250 mL-three necked round bottom flask, equipped with a nitrogen inlet, a mechanical stirrer and a distillation head, was charged with 152 g (2.0 moles) of 1,3-propanediol. Nitrogen gas was bubbled through the liquid for about 15 minutes and then 0.76 g (0.5 wt %) of concentrated sulfuric acid catalyst was added to the diol. The mixture was stirred mechanically and heated to 170–185° C. under a nitrogen blanket at atmospheric pressure. The water of reaction was removed by distillation and was collected continuously during the polymerization reaction. The reaction was continued for a period of 8 h, after which time the reaction mixture was cooled while maintaining the nitrogen atmosphere. The product thus obtained has a number average molecular weight of 830 as determined by NMR and an APHA color of 80.

Example 2

Preparation of Polytrimethylene Ether Glycol Using Sulfuric Acid Catalyst

A 250 mL-three necked round bottom flask, equipped with a nitrogen inlet, a mechanical stirrer and a distillation head, was charged with 152 g of 1,3-propanediol and 1.52 g (1.0 wt %) of concentrated sulfuric acid catalyst. The mixture was stirred mechanically and heated to 165–175° C. under nitrogen atmosphere. The water of reaction was removed by distillation and was collected. The reaction was continued for a period of 8.0 h. The crude sample was analyzed and the properties of the polyether are reported in Table 1.

Example 3

Preparation of Polytrimethylene Ether Glycol Using Sulfuric Acid Catalyst Under Reduced Pressure 1,3-Propanediol (152 g) and concentrated sulfuric acid (1.52 g) were placed in a 250 ml three necked round bottom flask and heated at 175° C. under nitrogen atmosphere for 1 h 40 min. During this period a total of 23.8 ml distillate was collected which corresponds to a DP of more than 2.5. At this stage, the flask was connected to a vacuum pump and the reaction was continued for a total period of time of 8 h. Initially the pressure was maintained at about 250 mm Hg (33 kPa) and then decreased to 1 mm Hg (130 Pa) and the reaction temperature was maintained at 175° C. The polyether glycol was analyzed and the polymer properties are compared with the polymer obtained from the Example 2 as shown in Table 1.

TABLE 1

Properties of Polytrimethylene Ether Glycols

| Property | Example 2 | Example 3 |
|---|---|---|
| Number average molecular weight (NMR) | 1,570 | 1,860 |
| Color | 5 Gardner | 110 APHA |

As can be seen from Table 1, the polymer prepared from the process where one stage was performed under reduced pressure, shows significant reduction in color as well as maintaining a reasonable higher molecular weight, suitable for use in elastomeric copolymers.

Example 4

Preparation of Polytrimethylene Ether Glycol Using Sulfuric Acid Catalyst Under Reduced Pressure 1,3-Propanediol (3.04 kg) and concentrated sulfuric acid (30.4 g) were placed in a 5 L three-neck round bottom flask fitted with a nitrogen inlet, mechanical stirrer and a distillation head. Nitrogen gas was bubbled through the reaction mixture for 15 min. The polymerization was carried out at 160° C. with stirring under nitrogen atmosphere. After collected 525 g of water distillate in a receiving flask, the flask was connected to a vacuum pump and the pressure was reduced slowly over a period of time to 1–5 mm Hg. The molecular weight of the reaction product was monitored by analyzing the samples at different time intervals using NMR end group analysis method. The polymerization was halted after obtaining the desired molecular weight (around 2000) and the product was purified as described below. Equal volume of water was added to the polymer and the reaction mixture was maintained at 90° C. for 16 hours and a stirring speed of 180 rpm under a nitrogen atmosphere. After 16 hours, the heater and the stirrer were turned off and the mixture was allowed to phase separate. The top aqueous phase was decanted and the polyether phase was washed further with distilled water three more times to extract out most of the acid and the oligomers. The residual acid left in the polyether glycol was neutralized with calcium hydroxide in excess. The polymer was dried at 100° C. under reduced pressure for 2–3 hours and then the dried polymer was filtered hot through a Whatman filter paper precoated with a Celite filter aid. The polyether glycol was analyzed and the polymer properties are listed in Table 2.

Example 5

Preparation of Polytrimethylene Ether Glycol

In a manner similar to Example 4 except the hydrolysis step was carried out 100° C. for 6 h. The crude polymer was purified as described in example 4 and the properties of the polymer are listed in Table 2.

TABLE 2

Properties of Purified Polytrimethylene Ether Glycols

| Example | 4 | 5 |
|---|---|---|
| Number average molecular weight | 2360 | 2452 |
| Hydroxyl number | 47.5 | 45.8 |
| Polydispersity (Mw/Mn (GPC) | 1.88 | 1.66 |
| Color (APHA) | 100 | 80 |
| Alkalinity, meqOH/30 kg | −1.35 | 0.5 |
| Unsaturation meq/kg | 12.5 | — |
| OCE, wt % | 0.65 | 0.91 |
| Viscosity @ 40° C., cP | 940 | 890 |
| Density @ 40° C., g/cc | 1.027 | 1.025 |
| Melting point, ° C. | 22.8 | 21.2 |
| Crystallization temperature, ° C. | −34 | −34 |
| Glass transition temperature (Tg), ° C. | −73 | −74 |

Examples 6–13

Preparation of Polytrimethylene Ether Glycol Using Acid Catalysts

In a manner similar to Example 1, polytrimethylene ether glycol was prepared employing a variety of dehydration catalysts and reaction conditions. Table 3 presents the results of the examples. Data presented include catalyst, quantity of catalyst, reaction temperature and time, pressure conditions and number average molecular weight of the resulting product.

TABLE 3

| Ex | Catalyst | Amount wt % | Reaction Temp. (° C.) | Reaction Time (h) | Atmospheric/ reduced pressure | $M_n$ |
|---|---|---|---|---|---|---|
| 6 | Sulfuric acid | 1.0 | 175–190 | 16.0 | Reduced[1] | 4480 |
| 7 | 1,1,1,2,3,3-Hexafluoropropane sulfonic acid | 1.0 | 180–190 | 4.45 | Atmospheric | 2184 |
| 8 | p-Toluenesulfonic acid | 1.25 | 190–200 | 5.0 | Atmospheric | 365 |
| 9 | Phosphorous acid | 2.0 | 210 | 26.0 | Atmospheric | 532 |
| 10 | 1,1,2,2-tetrafluoroethane sulfonic acid | 1.0 | 168–175 | 4.10 | Reduced[2] | 2967 |
| 11 | Phosphotungstic acid | 1.0 | 190–200 | 2.30 | Atmospheric | 462 |
| 12 | Lanthanum triflate | 2.0 | 190–195 | 8.0 | Atmospheric | 123 |
| 13 | 1,3-diiodopropane | 3.9 | 170–190 | 14.45 | Atmospheric | 719 |

[1]The pressures employed were 100 mm Hg down to 1 mm Hg (13 kPa to 130 Pa).
[2]The pressures employed were 250 mm Hg down to 100 mm Hg (33 kPa to 13 kPa).

Example 14

Preparation of Copolymer of 1,3-propanediol and 2, methyl,1,3-propanediol Using Sulfuric Acid Catalyst Under Reduced Pressure 1,3-Propanediol (136.8 g; 1.8 mol), 2-methyl-1,3-propanediol (18.0 g; 0.196 mol) and concentrated sulfuric acid (1.55 g) were charged to a 250 mL flask. The reaction mixture was heated at 175° C. under nitrogen atmosphere for 1h 40 min. During this period a total of 24.2 ml distillate was collected. At this stage, the flask was connected to a vacuum pump and the reaction was continued for a total period of time of 8 h and 10 min. Initially the pressure was maintained at about 250 mm Hg (33 kPa) and then decreased to 1 mm Hg (130 Pa) and the reaction temperature was maintained at 175° C.–190° C. The number average molecular weight of the copolymer was 2692 as determined from NMR.

Example 15

Preparation of Copolymer of 1,3-propanediol and 2-dimethyl-1,3-propanediol Using Sulfuric Acid Catalyst Under Reduced Pressure The procedure in Example 14 was followed, except that 21 g (0.2 mol) of 2,2-dimethyl-1,3-propanediol was used in place of ,2-methyl-1,3-propanediol. The number average molecular weight of the copolymer was 2690 as determined from NMR.

The foregoing disclosure of embodiments of the present invention has been presented for purposes of illustration and description. It is not intended to be exhaustive or to limit the invention to the precise forms disclosed. Many variations and modifications of the embodiments described herein will be evident to one of ordinary skill in the art in light of the above disclosure.

What is claimed is:

1. A process for the manufacture of polytrimethylene ether glycol comprising the steps of:

a) providing (1) 1,3-propanediol reactant selected from the group consisting of 1,3-propanediol and/or oligomers or prepolymers of 1,3-propanediol having a degree of polymerization of 2–9 and mixtures thereof, (2) 20 weight % or less of comonomer diol, and (3) a polycondensation catalyst; and b) polycondensing the 1,3-propanediol reactant and the 20 weight % or less of comonomer, diol to form a polytrimethylene ether glycol at less than one atmosphere pressure using the polycondensation catalyst.

2. The process of claim 1 wherein the 1,3-propanediol reactant is selected from the group consisting of 1,3-propanediol and/or dimer and trimer of 1,3-propanediol and mixtures thereof.

3. The process of claim 2 wherein the 1,3-propanediol reactant is selected from the group consisting of the 1,3-propanediol or the mixture containing at least 90 weight % of 1,3-propanediol.

4. The process of claim 2 wherein the 1,3-propanediol reactant is the 1,3-propanediol.

5. The process of claim 1 wherein polycondensation is carried out at a temperature of at least 150° C.

6. The process of claim 1 wherein the polycondensation temperature is no greater than 250° C.

7. The process of claim 1 wherein the polycondensation temperature is no greater than 210° C.

8. The process of claim 2 wherein the polycondensation temperature is no than greater than 210° C.

9. The process of claim 7 carried out in batch mode.

10. The process of claim 1 wherein the polycondensing pressure is less than 500 mm Hg (66 kPa).

11. The process of claim 1 wherein the polycondensing pressure is less than 250 mm Hg (33 kPa).

12. The process of claim 1 wherein the polycondensing pressure is less than 100 mm Hg (13 kPa).

13. The process of claim 1 wherein the polycondensing pressure is less than 50 mm Hg (6.6 kPa).

14. The process of claim 1 wherein the polycondensing pressure is less than 5 mm Hg (660 Pa).

15. The process of claim 8 wherein the polycondensing pressure is less than 250 mm Hg (33 kPa).

16. The process of claim 1 wherein the polytrimethylene ether glycol number average molecular weight is greater than 1,000.

17. The process of claim 16 wherein the number average molecular weight is greater than 1,500.

18. The process of claim 16 wherein the number average molecular weight is greater than 1,650.

19. The process of claim 16 wherein the number average molecular weight is greater than 2,000.

20. The process of claim 1 wherein the polytrimethylene ether glycol number average molecular weight is less than 5,000.

21. The process of claim 20 wherein the number average molecular weight is less than 4,000.

22. The process of claim 20 wherein the number average molecular weight is less than 3,500.

23. The process of claim 18 wherein the number average molecular weight is less than 5,000.

24. The process of claim 18 wherein the number average molecular weight is 4,950 or less.

25. The process of claim 1 further comprising purifying the polytrimethylene ether glycol to a dispersity of 1.5 to 2.1.

26. The process of claim 1 wherein the resulting polytrimethylene ether glycol has an APHA color of less than 120.

27. The process of claim 26 wherein the ALPHA color is less than 100.

28. The process of claim 26 wherein the ALPHA color is less than 30.

29. The process of claim 1 further comprising purifying the polytrimethylene ether glycol to an unsaturation of less than 20 meq/kg.

30. The process of claim 29 wherein the unsaturation is as than 15 meq/kg.

31. The process of claim 1 wherein the resulting polytrimethylene ether glycol has a content of cyclic ether oligomers of less than 2 weight %.

32. The process of claim 1 further comprising purifying the polytrimethylene ether glycol to a cyclic ether oligomer content less than 1 weight %.

33. A process for the manufacture of polytrimethylene ether glycol comprising the steps of:
   a) providing (1) 1,3-propanediol, (2) 1–20 mole %, based on all diols present, of comonomer diol, and (3) polycondensation catalyst; and
   b) polycondensing the 1,3-propanediol and the comonomer diol to form a polytrimethylene ether glycol at less than one atmosphere pressure using the polycondensation catalyst.

34. The process of claim 33 wherein the comonomer diol is selected from the group consisting of 2-methyl-1,3-propanediol, 2,2-dimethyl-1,3-propanediol, 2,2-diethyl-1,3-propanediol, 1,6-hexanediol, 1,8-octanediol, 1,10-decanediol, 1,12-dodecanediol and mixtures thereof.

35. The process of claim 33 wherein the comonomer diol is selected from the group consisting of 2-methyl-1,3-propanediol, 2,2-dimethyl-1,3-propanediol, and 2,2-diethyl-1,3-propanediol.

36. The process of claim 1 wherein the 1,3-propanediol reactant is the 1,3-propanediol and the 1,3-propanediol has a purity greater than 99%.

37. The process of claim 1 wherein the 1,3-propanediol reactant comprises the 1,3-propanediol and up to 10% of the low molecular eight oligomers.

38. The process of claim 1 wherein the polytrimethylene ether glycol has a number average molecular weight of 1,500–4,950 and an APHA color of less than 120, the pressure in the reduced pressure stage is less than 250 mm Hg (33 kPa) and the polycondensation temperature is 170–190° C.

39. A process for the manufacture of polytrimethylene ether glycol comprising the steps of:
   a) providing (1) 1,3-propanediol, (2) 20 weight % or less of comonomer diol, and (3) a polycondensation catalyst;
   b) condensing 1,3-propanediol and the 20 weight % or less of comonomer diol to form oligomer or prepolymer of 1,3-propanediol having a degree of polymerization of 2–9 or a mixture thereof using the polycondensation catalyst; and
   c) polycondensing the oligomer or prepolymer of 1,3-propanediol having a degree of polymerization of 2–9 or a mixture thereof, to form a polytrimethylene ether glycol at less than a atmosphere pressure using the polycondensation catalyst.

40. The process of claim 39 wherein step b) is carried out at about atmospheric pressure, the pressure in step c) is less than 300 mm Hg (40 kPa), the temperature in step b) is 150–210° C. and the temperature in step c) is 170–250° C.

41. The process of claim 40 wherein the temperature in step b) is 170–210° C. and the temperature in step c) is 180–210° C.

42. The process of claim 41 wherein in step b), 1,3-propanediol is condensed to dimer and trimer.

43. The process of claim 41 wherein the pressure for step c) is less than 250 mm Hg (33 kPa) and the polytrimethylene ether has a number average molecular weight of 1,650 to 4,950.

44. Polytrimethylene ether glycol produced by the process of claim 1, having a number average molecular weight of greater than 1,500 and a dispersity of 1.5 to 2.1.

45. The polytrimethylene ether glycol of claim 44 having a number average molecular weight of greater than 1,650.

46. Polytrimethylene ether glycol having a number average molecular weight greater than 1,500, an APHA color of less than 120, an unsaturation of less than 20 meq/kg, and a content of cyclic ether oligomer of less than 2 weight %.

47. The polytrimethylene ether glycol of claim 46 having a dispersity of 1.5 to 2.1 and an alkalinity in the range of −2 to +1.

48. The polytrimethylene ether glycol of claim 47 having a number average molecular weight of from 1,650 to 4,000.

49. The polytrimethylene ether glycol of claim 48 having an APHA color of less than 100, an unsaturation of less than 15 meq/kg and a cyclic ether content of less than 1 weight %.

50. The process of claim 1 wherein the comonomer diol is selected from the group consisting of aliphatic diols, cycloaliphatic diols, and polyhydroxy compounds, and mixtures thereof.

51. The process of claim 1 wherein the comonomer diol is selected from the group consisting of 1,6-hexanediol, 1,7-heptanediol, 1,8-octanediol, 1,9-nonanediol, 1,10-decanediol, 1,12-dodecanediol, 3,3,4,4,5,5-hexafluro-1,5-pentanediol, 2,2,3,3,4,4,5,5-octafluoro-1,6-hexanediol, 3,3,4,4,5,5,6,6,7,7,8,8,9,9,10,10-hexadecafluoro-1,12-dodecanediol, cycloaliphatic diols, polyhydroxy compounds, trimethylolpropane, and pentaerythritol, and mixtures thereof.

52. The process of claim 1 wherein the comonomer diol is selected from the group consisting of 2-methyl-1,3-propanediol, 2,2-dimethyl-1,3-propanediol, 2,2-diethyl-1,3-propanediol, 2-ethyl-2-(hydroxymethyl)-1,3-propanediol, 1,6-hexanediol, 1,8-octanediol, 1,10-decanediol, isosorbide, and mixtures thereof.

53. The process of claim 1 carried out without the comonomer diol.

54. The process of claim 1 further comprising purifying the polytrimethylene ether glycol.

55. The process of claim 1 further comprising purifying the polytrimethylene ether glycol by hydrolyzing the acid esters present in its polymer chain and removing at least one of unreacted glycol, and linear and cyclic ether a oligomer.

56. The process of claim 1 further comprising purifying the polytrimethylene ether glycol by a process comprising: hydrolysis of acid esters that are formed during the polycondensation; water extraction steps to remove acid, unreacted monomer, low molecular weight linear oligomers and oligomers of cyclic ethers; solid base treatment to neutralize residual acid present; and drying and filtration of the polytrimethylene ether glycol to remove residual water and solids.

57. The process of claim 2 wherein the polytrimethylene ether glycol number average molecular weight is greater than 1,000.

58. The process of claim 2 wherein the number average molecular weight is greater than 1,500.

59. The process of claim 57 wherein the polytrimethylene ether glycol number average molecular weight is less than 5,000.

60. The process of claim 59 further comprising purifying the polytrimethylene ether glycol to a dispersity of 1.5 to 2.1.

61. The process of claim 60 wherein the resulting polytrimethylene ether glycol has an ALPHA color of less than 120.

62. The process of claim 61 further comprising purifying the polytrimethylene ether glycol to an unsaturation of less than 15 meq/kg.

63. The process of claim 36 wherein the polytrimethylene ether glycol number average molecular weight is greater than 1,000.

64. The process of claim 36 wherein the number average molecular weight is greater than 1,500.

65. The process of claim 57 wherein the polytrimethylene ether glycol number average molecular weight is less than 5,000.

66. The process of claim 39 wherein the comonomer diol is selected from the group consisting of aliphatic diols, cycloaliphatic diols, and polyhydroxy compounds, and mixtures thereof.

67. The process of claim 39 wherein the comonomer diol is selected from the group consisting of 1,6-hexanediol, 1,7-heptanediol, 1,8-octanediol, 1,9-nonanediol, 1,10-decanediol, 1,12-dodecanediol, 3,3,4,4,5,5-hexafluro-1,5-pentanediol, 2,2,3,3,4,4,5,5-octafluoro-1,6-hexanediol, 3,3,4,4,5,5,6,6,7,7,8,8,9,9,10,10-hexadecafluoro-1,12-dodecanediol, cycloaliphatic diols, polyhydroxy compounds, trimethylolpropane, and pentaerythritol, and mixtures thereof.

68. The process of claim 39 wherein the comonomer diol is selected from the group consisting of 2-methyl-1,3-propanediol, 2,2-dimethyl-1,3-propanediol, 2,2-diethyl-1,3-propanediol, 2-ethyl-2-(hydroxymethyl)-1,3-propanediol, 1,6-hexanediol, 1,8-octanediol, 1,10-decanediol, isosorbide, and mixtures thereof.

69. The process of claim 39 carried out without the comonomer diol.

70. The process of claim 39 further comprising purifying the polytrimethylene ether glycol.

71. The process of claim 39 further comprising purifying the polytrimethylene ether glycol by hydrolyzing acid esters present in its polymer chain and removing at least one of unreacted glycol, and linear and cyclic ether oligomer.

72. The process of claim 39 further comprising purifying the polytrimethylene ether glycol by a process comprising: hydrolysis of acid esters that are formed during the polycondensation; water extraction steps to remove acid, unreacted monomer, low molecular weight linear oligomers and oligomers of cyclic ethers; solid base treatment to neutralize residual acid present; and drying and filtration of the polytrimethylene ether glycol to remove residual water and solids.

73. Polytrimethylene ether glycol as claimed in claim 44, having an APHA color of less than 120 and an unsaturation of less than 15 meq/kg.

74. A process for the manufacture of polytrimethylene ether glycol comprising the steps of:

a) providing (1) 1,3-propanediol, (2) 1–20 mole %, based on all diols present, of comonomer diol, and (3) polycondensation catalyst;

b) condensing 1,3-propanediol and the comonomer diol to form oligomer or prepolymer of having a degree of polymerization of 2–9 or a mixture thereof using the polycondensation catalyst; and c) polycondensing the oligomer or prepolymer, to form a polytrimethylene ether glycol at less than one atmosphere pressure using the polycondensation catalyst.

75. The process of claim 74 wherein step b) is carried out at about atmospheric pressure, the pressure in step c) is less than 300 mm Hg (40 kPa), the temperature in stop b) is 150–210° C. and the temperature in step c) is 170–250° C.

76. The process of claim 74 wherein the comonomer diol is selected from the group consisting of 2-methyl-1,3-propanediol, 2,2-dimethyl-1,3-propanediol, 2,2-diethyl-1,3-propanediol, 1,6-hexanediol, 1,8-octanediol, 1,10-decanediol, 1,12-dodecanediol and mixtures thereof.

77. The process of claim 74 wherein the comonomer diol is selected from the group consisting of 2-methyl-1,3-propanediol, 2,2-dimethyl-1,3-propanediol, and 2,2-diethyl-1,3-propanediol.

78. The process of claim 33 wherein the polytrimethylene ether glycol has a number average molecular weight of 1,500–4,950 and an ALPHA color of less than 120, the pressure in the reduced pressure stage is less than 250 mm Hg (33 kPa) and the polycondensation temperature is 170–190° C.

79. Polytrimethylene ether glycol having a number average molecular weight greater than 1,500, an APHA color of less than 120, and an unsaturation of less than 15 meq/kg.

80. Polytrimethylene ether glycol produced by the process of claim 39, having a number average molecular weight of greater than 1,500 and a dispersity of 1.5 to 2.1.

81. The polytrimethylene ether glycol of claim 44 having a number average molecular weight of greater than 1,650.

82. Polytrimethylene ether glycol as claimed in claim 46, having an unsaturation of less than 15 meq/kg.

83. The polytrimethylene ether glycol of claim 82 having a dispersity of 1.5 to 2.1 and an alkalinity in the range of −2 to +1.

84. The polytrimethylene ether glycol of claim 83 having a number average molecular weight of from 1,650 to 4,000.

85. The polytrimethylene ether glycol of claim 84 having APHA color of less than 100, an unsaturation of less than 15 meq/kg and a cyclic ether content of less than 1 weight %.

86. Polytrimethylene ether glycol produced by the process of claim 33, having a number average molecular weight of greater than 1,500 and a dispersity of 1.5 to 2.1.

87. Polytrimethylene ether glycol produced by the process claim 74, having a number average molecular weight of greater than 1,500 and a dispersity of 1.5 to 2.1.

\* \* \* \* \*